United States Patent
Godfrey

(10) Patent No.: US 9,561,812 B2
(45) Date of Patent: Feb. 7, 2017

(54) MONITORING TRANSPORT NETWORK INFRASTRUCTURE

(71) Applicant: OPTASENSE HOLDINGS LIMITED, Farnborough, Hampshire (GB)

(72) Inventor: Alastair Godfrey, Farnborough (GB)

(73) Assignee: OPTASENSE HOLDINGS LIMITED (GB)

( * ) Notice: Subject to any disclaimer, the term of this patent is extended or adjusted under 35 U.S.C. 154(b) by 171 days.

(21) Appl. No.: 14/380,130

(22) PCT Filed: Feb. 22, 2013

(86) PCT No.: PCT/GB2013/050451
§ 371 (c)(1),
(2) Date: Aug. 21, 2014

(87) PCT Pub. No.: WO2013/124681
PCT Pub. Date: Aug. 29, 2013

(65) Prior Publication Data
US 2015/0013465 A1   Jan. 15, 2015

(30) Foreign Application Priority Data
Feb. 24, 2012 (GB) .................................. 1203273.6

(51) Int. Cl.
*G01N 29/04* (2006.01)
*B61L 23/04* (2006.01)
(Continued)

(52) U.S. Cl.
CPC .............. *B61L 23/04* (2013.01); *B61L 23/044* (2013.01); *B61L 23/045* (2013.01); *B61L 23/047* (2013.01);
(Continued)

(58) Field of Classification Search
CPC .... G01M 5/00; G01M 5/0008; G01M 5/0066; G01M 5/0041; G01M 5/0091; G01M 5/0025; G01N 29/04; B61L 23/04; B61L 23/045; B61L 23/047; B61L 23/048; B61L 23/044
See application file for complete search history.

(56) References Cited

U.S. PATENT DOCUMENTS 4,654,520 A * 3/1987 Griffiths ................. G01B 11/18
250/227.14
4,812,645 A * 3/1989 Griffiths ................. G01B 11/18
250/227.14

(Continued)

FOREIGN PATENT DOCUMENTS

EP       1902923         3/2008
WO    WO 2010/116119    10/2010
(Continued)

OTHER PUBLICATIONS

Kawano et al., "Health Monitoring of a Railway Bridge by Fiber Optic Sensor (SOFO)", retrieved from internet: URL: http:///www.roctest-group.com/sites/default/files/bibliography/pdf/C213.pdr, retrieved on Feb. 17, 2014.

(Continued)

*Primary Examiner* — Helen Kwok
(74) *Attorney, Agent, or Firm* — McDonnell Boehnen Hulbert & Berghoff LLP

(57) ABSTRACT

The present invention relates to conditions monitoring of structures forming part of a transport network, e.g. structural health monitoring of structures, especially tunnels by performing distributed acoustic sensing (DAS) on at least one optical fiber (104) deployed so as to monitor the structure (206) and detecting and analyzing the acoustic response to movement of traffic (205) on the network in the vicinity of the structure to detect the acoustic response (303, 304) of the (Continued)

structure. The acoustic response of the structure is then analyzed to detect any change in condition.

20 Claims, 6 Drawing Sheets

(51) Int. Cl.
    *B61L 27/00*     (2006.01)
    *G01M 5/00*     (2006.01)
    *B61L 1/16*     (2006.01)

(52) U.S. Cl.
    CPC .......... *B61L 23/048* (2013.01); *B61L 27/0088* (2013.01); *G01M 5/0025* (2013.01); *G01M 5/0033* (2013.01); *G01M 5/0066* (2013.01); *G01M 5/0091* (2013.01); *G01N 29/04* (2013.01); *B61L 1/166* (2013.01)

(56) References Cited

U.S. PATENT DOCUMENTS

| | | | | |
|---|---|---|---|---|
| 5,056,884 A | * | 10/1991 | Quinlan, Jr. | G01L 1/242 385/13 |
| 5,250,802 A | * | 10/1993 | Runner | G01M 11/086 250/227.15 |
| 5,330,136 A | | 7/1994 | Colbaugh | |
| 5,529,267 A | * | 6/1996 | Giras | B61L 23/047 246/120 |
| 5,600,133 A | * | 2/1997 | Spillman, Jr. | G01N 29/2418 250/227.14 |
| 5,743,495 A | * | 4/1998 | Welles, II | B61L 23/047 246/121 |
| 5,895,843 A | * | 4/1999 | Taylor | H01C 10/46 324/700 |
| 6,476,377 B1 | * | 11/2002 | Hodge | G01D 5/34 250/227.11 |
| 6,487,914 B1 | | 12/2002 | Hodge | |
| 6,647,161 B1 | * | 11/2003 | Hodge | G01B 11/16 385/12 |
| 7,777,496 B2 | * | 8/2010 | Evans | G01N 21/84 324/534 |
| 8,144,333 B2 | * | 3/2012 | Huffman | G01M 5/00 356/480 |
| 2006/0202860 A1 | | 9/2006 | Tsai et al. | |
| 2010/0158431 A1 | | 6/2010 | Huffman et al. | |
| 2010/0242609 A1 | | 9/2010 | Lee et al. | |
| 2011/0075964 A1 | | 3/2011 | Huffman | |

FOREIGN PATENT DOCUMENTS

| | | |
|---|---|---|
| WO | WO 2010136764 | 12/2010 |
| WO | WO 2011/058312 | 5/2011 |
| WO | WO 2011058314 | 5/2011 |
| WO | WO 2012/022934 | 2/2012 |

OTHER PUBLICATIONS

Krohn et al., "Fiber Optic Sensor Applications in Transportation Infrastructure Protection", Proceedings of SPIE, vol. 7314, Apr. 29, 2009.

\* cited by examiner

MONITORING TRANSPORT NETWORK INFRASTRUCTURE

FIELD OF THE INVENTION

The present invention relates to monitoring of infrastructure of transport networks, for example infrastructure of rail networks, such as tunnels or bridges or the rail track itself, and in particular to condition monitoring which uses movement of traffic on the rail network.

BACKGROUND OF THE INVENTION

Transport network infrastructure, such as rail network infrastructure, will typically comprise some structures that it is desirable to monitor the condition of. For instance it may be desired to monitor the condition of tunnels that form part of the network to detect any faults in the tunnel that could lead to failure.

In some rail networks the condition of tunnels may be manually inspected. This may comprise an inspection by suitable personnel, including a visual inspection and/or performance of various tests or measurements to identify any potential problems. For instance, the condition of the walls may be visually inspected, the relative position of known markers measured for any movement and in some instances the wall condition may be tested using suitable probes.

Clearly however such inspections require sending an inspection team to the relevant structure and the inspection can take significant time. The area to be inspected, even in a single track rail tunnel of a few hundred meters in length, may be significant and some tunnels may large enough to house multiple tracks and be of the orders of kilometers in length. The inspection may only be possible in times when the relevant section of rail network is not in use, which may limit the time available for inspection and/or result in reduced or cancelled services on the network. For these reasons manual inspection is typically a time consuming and costly undertaking and most infrastructure is therefore inspected only periodically, in some instances with significant periods of time between inspections.

In some structures there may also be a number of permanently installed sensors to provide on-going structural health monitoring. For instance various strain sensors, accelerometers etc. and the like may be deployed through a tunnel to detect any motion. Such sensors are typically point sensors and thus providing adequate coverage for a tunnel, which may be kilometers in length, requires many such sensors with consequent expense. For remote monitoring each sensor must have a suitable power supply and be arranged to be able to transmit the acquired data for analysis.

SUMMARY OF THE INVENTION

Embodiments of the present invention provide methods and apparatus for condition monitoring of structures forming part of the infrastructure of a transport network.

In one aspect of the invention there is provided a method of condition monitoring of a structure forming part of a transport network, the method comprising: performing distributed acoustic sensing on one or more optical fibres deployed to monitor said structure to provide a measurement signal from each of a plurality of acoustic sensing portions; analysing the measurement signals generated from movement of traffic on the transport network in the vicinity of said structure to identify acoustic signals associated with said structure; and analysing said acoustic signals associated with said structure to provide an indication of any changes in condition of said structure.

The method of this aspect of the present invention uses fibre optic distributed acoustic sensing (DAS). Distributed acoustic sensing is a known type of sensing where an optical fibre is deployed as a sensing fibre and repeatedly interrogated with electromagnetic radiation to provide sensing of acoustic activity along its length. Typically one or more input pulses of radiation are launched into the optical fibre. By analysing the radiation backscattered from within the fibre, the fibre can effectively be divided into a plurality of discrete sensing portions which may be (but do not have to be) contiguous. Within each discrete sensing portion mechanical disturbances of the fibre, for instance due to incident acoustic waves, cause a variation in the properties of the radiation which is backscattered from that portion. This variation can be detected and analysed and used to give a measure of the intensity of disturbance of the fibre at that sensing portion. Thus the DAS sensor effectively acts as a linear sensing array of acoustic sensing portions of optical fibre. The length of the sensing portions of fibre is determined by the characteristics of the interrogating radiation and the processing applied to the backscatter signals but typically sensing portions of the order of a few meters to a few tens of meters or so may be used. As used in this specification the term "distributed acoustic sensing" will be taken to mean sensing by interrogating an optical fibre to provide a plurality of discrete acoustic sensing portions distributed longitudinally along the fibre and the term "distributed acoustic sensor" shall be interpreted accordingly. The term "acoustic" shall mean any type of pressure wave or mechanical disturbance that may result in a change of strain on an optical fibre and for the avoidance of doubt the term acoustic be taken to include ultrasonic and subsonic waves as well as seismic waves.

DAS can be operated to provide many sensing portions or channels over a long length of fibre, for example DAS can be applied on fibre lengths of up to 40 km or more with contiguous sensing channels of the order of 10 m long.

In co-pending patent application GB1201768.7 it has been proposed that DAS sensors may be deployed along transport networks, such as rail or road networks, to provide monitoring of traffic movement on the transport network as part of a control method and/or to detect abnormal traffic movement. For instance in a rail network, movement of a train on a train track adjacent a DAS sensing fibre will generate acoustic signals that can be used to track the train as it moves, providing real time positional information to a resolution of a few tens of meters continuously along the entire length of the monitored section.

The present inventors have realised that DAS can be used to provide condition monitoring of a structure forming part of or associated with a transport network by monitoring the acoustic response of the structure to the passage of traffic on the network. The present inventors have identified that movement of traffic on the network provides acoustic excitation of the structure and that the response of the structure itself can be discriminated from the general noise of the traffic. In other words the traffic movement provides an acoustic source and, surprisingly, the acoustic signals associated with the structure itself can be separately identified as distinct from the acoustic source. Further the inventors have realised that acoustic response of a structure to the passage of traffic may be largely the same even when the traffic differs. In other words, taking the example of monitoring a tunnel on a rail network, the passage of a first train through the tunnel excites the same general response in the tunnel as subsequently the passage of another train through the same tunnel. The transport network may be a network for the vehicular movement of people and/or goods and may in particular be a rail network.

It has therefore been appreciated that the acoustic response of the structure can be monitored during network operation to provide ongoing condition monitoring. Any significant changes in acoustic response may indicate a change in condition.

The method therefore involves performing distributed acoustic sensing on at least one optical fibre to provide a measurement signal from each of a plurality of acoustic sensing portions as described above. The at least one sensing fibre is deployed so as to monitor the structure. The sensing fibre may be deployed to run through a structure such as a tunnel, bridge, viaduct, embankment or cutting and, in some instances, at least part of the fibre may be embedded within the material of the structure. In other applications however a sensing fibre may additionally or alternatively be deployed with at least part of the optical fibre adjacent to the structure or attached to the structure.

As mentioned previously the measurement signals generated from movement of traffic, i.e. vehicles, on the transport network in the vicinity of said structure are analysed to identify acoustic signals associated with said structure, i.e. to distinguish those signals due to the acoustic response of the structure from any signals directly due to traffic movement. As will be described later this may be achieved in various ways.

The acoustic signals which are identified as being associated with the structure are then analysed to provide an indication of any changes in condition of said structure.

In one embodiment analysing the acoustic signals associated with said structure comprises comparing the acoustic signals with previously acquired acoustic signals. As described previously the general acoustic response of the structure may be the same for generally the same type of traffic movement, e.g. trains travelling in the same direction through a tunnel may excite the same general response if there has been no significant change in tunnel conditions. In effect therefore the structure may exhibit an acoustic signature.

For example consider a tunnel which is 300 m in length say with a DAS sensing optical fibre running through the tunnel and interrogated so as to provide sensing portions of the order of 15 m in length. There may therefore be 20 contiguous sensing portions of fibre along the length of the tunnel. In response to a train passing through the tunnel some sensing portions may typically exhibit an acoustic response which is more intense and/or persists for longer than other sensing portions. In addition some sensing portions may exhibit strong responses at some acoustic frequencies compared to others. Thus the patterns of relative intensity, time evolution and/or frequencies of the measurement signals from the various sensing portions corresponding to the structure may be seen as an acoustic signature for the structure, in this example the tunnel.

The acoustic signature detected in response to movement of traffic near the structure could then be compared to a pre-existing signature corresponding to or derived from one or more previously detected responses. If the most recently acquired acoustic signature is substantially the same as the pre-existing signature this may be taken as an indication that the properties of the structure are the same and thus the condition of the structure has not changed. However if, for example, a sensing portion exhibits an acoustic response which has a markedly different relative intensity or duration than previously this could indicate a change in properties of the structure, which could potentially indicate a change in the condition of the structure.

In some embodiments analysing the acoustic signals associated with the structure may comprise identifying acoustic waves propagating in the structure. Especially for elongate structures, i.e. structures such as tunnels that extend for some distance and thus may extend for several sensing portions of the DAS sensor, the propagation of acoustic waves within the structure may be identified. Typically the acoustic energy generated by traffic moving along a structure such as a tunnel will lead to acoustic waves propagating along the structure. This will lead to a series of disturbances of the fibre which will be detected by the DAS sensor as an acoustic signal affecting the various sensing portions in sequence. The propagation of such acoustic waves may form at least part of the acoustic signature of the structure and may be compared to previously detected responses to detect any significant change.

In particular the method may involve identifying any discontinuities in acoustic waves propagating in the structure, for example a sudden change in velocity or intensity of the wave or detection of a reflection.

To take a simple example, consider that a structure comprises a homogeneous solid material. Any acoustic wave propagating within such a structure may be expected to travel at a relatively constant speed (subject to any multipath effects) and with a relatively constant attenuation. If however there is a discontinuity, such as a crack or void within the material, there may be a step change in velocity or intensity at the crack or void and/or significant reflections may be generated. The step change and/or reflections could be detected indicating a potential problem at the location of the relevant sensing portion—especially if such step change or reflections had not previously been detected.

The method may therefore comprise analysing the propagation speeds of acoustic waves in the structure.

Note that the propagation speed of acoustic waves propagating in the structure may be different to the propagation speed of acoustic waves in air. Thus detecting a propagation speed which is different to that from air may be used to detect the signals propagating in the structure.

Also the propagation speed of acoustic waves in the structure which it is wished to monitor may be different to the propagation speed of acoustic waves in other structure forming the transport network. For example consider a rail network. There will be rails forming the railway along the whole of transport network. As a train travels on the network at least some acoustic signals may propagate through the rails at a speed determined by the composition of the rails (and possibly environmental effects). When the train reaches a tunnel some acoustic signals may propagate through the tunnel at a different speed to any signals travelling through air or through the rails. Detection of signals propagating at different speeds may be used to discriminate between those signals propagating through the structure of interest and any other network structure.

The method may also comprise identifying acoustic waves propagating at different speeds in the structure. Typically a structure may comprise various different materials. For instance there may be mix of some or all of concrete filings, brickworks, steel beams etc. all of which will exhibit a different speed of sound. Thus an acoustic wave propagating along an elongate structure may travel at different speeds in different parts of the structure. By looking at the speed of the acoustic wave as it propagates along the structure it may be possible to detect the acoustic signals from different parts of the structure. If the various components of the structure are known it may therefore be possible to discriminate between the acoustic response of different materials within the structure.

The method may therefore comprise analysing the measurement signals from the sensing portions to detect acoustic signals propagating along the structure at predefined speeds or within a predefined range of speeds. In other words when analysing the returns from a structure having significant amounts of concrete the method may comprise looking for signals propagating at the speed of sound in concrete.

Looking for particular expected propagation speeds can aid in distinguishing the acoustic response of the structure from the direct noise of the traffic which is detected by the DAS sensor.

In one embodiment however the acoustic response from the structure is detected by looking at the measurement signals which are recorded before and/or after the traffic passes the relevant sensing portion(s). Thus the acoustic signals associated with the structure are those detected by the sensing portions before and/or after the traffic movement past the relevant sensing portion.

As traffic moves on a network, such as a train moving on a rail track, the noise generated by the train will propagate in front and behind of the moving train. Thus as the traffic approaches a structure, especially an enclosed structure such as a tunnel, the sound of the moving traffic, e.g. train, will acoustically stimulate the structure. As mentioned above the acoustic energy will couple to the structure and, for an elongate structure such as a tunnel, will propagate along the tunnel. At this point the acoustic signals detected by the DAS sensor will comprise largely the acoustic response of the structure to a stimulus coming from a defined direction. This allows the acoustic response of the structure itself to be determined. Once the train actually reaches the relevant sensing portions however the fibre will be directly stimulated from several different directions from different parts of the train and all sensing portions will typically exhibit an intense response. Thus any influence of the structure on the acoustic response may be swamped by the 'direct' disturbance caused by the train. Once the train has passed the relevant sensing portions however the acoustic source will again become more directional. In addition the acoustic excitation of the structure due to passage of the train may take some time to subside and thus acoustic response following passage of the train will also be largely due to the acoustic response of the structure.

As well the general noise created by the traffic as it moves, high speed traffic can also produce a pressure impulse on nearby structures, especially portals such as bridges or tunnels. As a high speed train reaches a tunnel the air pressure will increase due to the motion of the train. As the train passes the air pressure will then reduce. This can create a pressure impulse which acoustically excites the structure. The acoustic response of the structure to such a pressure impulse can be monitored as described above.

In addition by looking at the low frequency response of the DAS sensor the increase and decrease in strain caused by the increase and decrease in air pressure may be detected, which may provide information about the condition of the structure.

As mentioned previously the optical fibre used for DAS is deployed so as to monitor the structure, which may involve the optical fibre being arranged to run through a structure such as a tunnel or bridge. The optical fibre could be a dedicated optical fibre which has been deployed specifically for monitoring of the structure or could be an optical fibre which had previously been deployed for some other purposes but which is suitable for use as a sensing fibre in a DAS system. For example in a tunnel there may be existing fibre optic cables intended for communications which may have redundant optical fibres that can be used for DAS.

In some embodiments at least one sensing fibre may form part of a DAS monitoring system used for monitoring and/or control of movement of traffic on the transport network. As mentioned previously DAS is well suited to monitoring movement of traffic on a transport network, especially movement of rail vehicles on a rail network. A single DAS sensor can provide a contiguous series of sensing channels separated by 10 m or so for a length of up to 40 km or more and greater lengths can achieved by using more sensors. A single DAS interrogator unit may be multiplexed between two fibres to provide sensing over a distance of 80 km (with the interrogator in the middle) with the fibres deployed along the path of the network. This offers the ability for continuity of sensing along large parts of the network. The sensing fibre may be standard telecoms fibre and thus is relatively cheap. The fibre may be simply buried alongside the transport networks, e.g. along the sides or underneath tracks or roads in a narrow channel at any depth required. The optical fibre can be encased in a protective casing and can survive for a long time with no maintenance. Thus installation and maintenance costs are low. In many transport networks there may already be optic fibre deployed along at least the major routes and such existing communications infrastructure may comprise redundant optical fibres that can be used for DAS.

The optical fibre is interrogated by optical pulses generated by the interrogator unit (as will be explained in more detail later) and thus power is only needed for the interrogator units.

Thus the sensing fibre may be deployed along the path of the transport network and used to track the movement of traffic on the network. In addition, in the vicinity of structures which it is wished to monitor the condition of, the acoustic signals associated with the structure may be detected and analysed as set out above. The deployment of the fibre may therefore simply be to follow the general path of the network, e.g. be laid alongside the rail track. For some structures however, e.g. bridges, a first section of fibre could be deployed alongside the path of the transport network until the structure is reaches, at which point a second section of fibre could be deployed in relation to the structure to provide sensing of the structure, before continuing along the rest of the path of the network. Thus the second section of fibre may be arranged to be attached to the bridge say. The fibre before and after the second section may be deployed to run alongside the path of the transport network and the measurement signals from these sensing portions can be used to track traffic motion of traffic on the network. However the returns from the first section will give useful information about the condition of the structure.

As mentioned the method is particularly applicable to rail networks and thus the optical fibre may be deployed alongside a rail network. The method is also particularly useful for monitoring the condition of tunnels. The optical fibre may therefore be deployed alongside a rail track running through the tunnel.

In some embodiments the structure to be monitored may include the rail track itself. As mentioned above the noise from the train will travel ahead or the train and behind the train for some distance. Some of this noise will be carried by acoustic waves propagating in the rails and the propagation of this acoustic signal through the rails will give an indication of the condition of the rails themselves and underlying track. The expected propagation speed of acoustic signals through the rails may be known and the thus the acoustic signals in front of and behind the moving train may be analysed to detect the signals propagating within the expected range of speeds as described previously. As describe however the method of the present invention allows structure which is separate from the rail track to be monitored using the passage of trains on the track, without requiring any direct active stimulus of the structure. In the case of tunnels the structure being monitored is not structure over which the vehicle of the transport network travel.

The method also extends to the processing of data from a DAS system to provide condition monitoring. Thus in another aspect of the invention there is provided a method of condition monitoring of structures forming part of a transport network, the method comprising receiving a plurality of measurement signals acquired by a one or more distributed acoustic sensors having one or more optical fibres deployed to monitor said structure; analysing the measurement signals generated from movement of traffic on the transport network in the vicinity of said structure to identify acoustic signals associated with said structure; and analysing said acoustic signals associated with said structure to provide an indication of any changes in condition of said structure.

The method according to this aspect of the invention thus receives data which has been acquired by DAS and analyses such data as described previously. It thus operates in all of the same ways and offers all of the same advantages as the first aspect of the invention.

Aspects of the invention also relate to a computer program or computer readable storage medium comprising computer readable code, which when executed on a suitable computing device, implements any of the methods described above.

The invention also relates to a distributed acoustic sensing system comprising an interrogator unit for, in use, performing distributed acoustic sensing on one or more optical fibres deployed to monitor a structure of a transport network to provide a measurement signal from each of a plurality of acoustic sensing portions; and a processor configured to analyse the measurement signals generated from movement of traffic on the transport network in the vicinity of said structure to identify acoustic signals associated with said structure; and analyse said acoustic signals associated with said structure to provide an indication of any changes in condition of said structure.

The system according to this aspect of the present invention offers all of the same advantages and can be used in all of the same ways as the methods described above.

The system, in use will comprise an optical fibre deployed to monitor the structure and at least part of the optical fibre may be deployed along the path of a transport network. The transport network may be a rail network and the system may be configured to monitor the condition of one or more tunnels on the network. The system may also be used to track the movement of traffic on the network and/or to provide one or more control signals for controlling movement of traffic on the network. The invention also provides a transport network control system comprising such a distributed acoustic sensing system.

DESCRIPTION OF THE DRAWINGS

The invention will now be described, by way of example only, with reference to the following drawings, of which.

DESCRIPTION OF THE INVENTION

Figure 1:
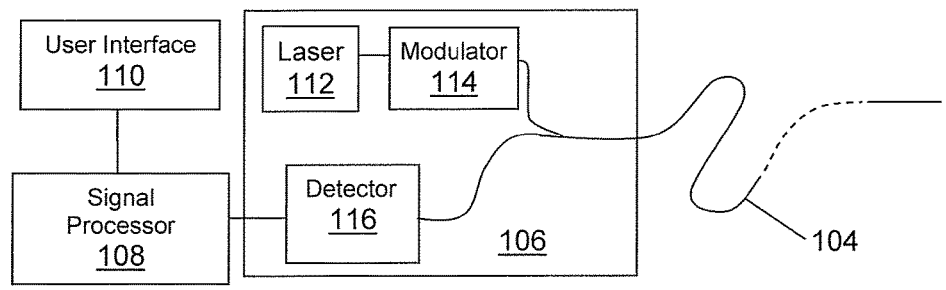
FIG. 1 shows a conventional DAS sensor arrangement.

FIG. 1 shows a schematic of a distributed fibre optic sensing arrangement. A length of sensing fibre 104 is removably connected at one end to an interrogator 106. The output from interrogator 106 is passed to a signal processor 108, which may be co-located with the interrogator or may be remote therefrom, and optionally a user interface/graphical display 110, which in practice may be realised by an appropriately specified PC. The user interface may be co-located with the signal processor or may be remote therefrom.

The sensing fibre 104 can be many kilometers in length and can be, for instance 40 km or more in length. The sensing fibre may be a standard, unmodified single mode optic fibre such as is routinely used in telecommunications applications without the need for deliberately introduced reflection sites such a fibre Bragg grating or the like. The ability to use an unmodified length of standard optical fibre to provide sensing means that low cost readily available fibre may be used. However in some embodiments the fibre may comprise a fibre which has been fabricated to be especially sensitive to incident vibrations. The fibre will be protected by containing it with a cable structure. In use the fibre 104 is deployed in an area of interest to be monitored.

In operation the interrogator 106 launches interrogating electromagnetic radiation, which may for example comprise a series of optical pulses having a selected frequency pattern, into the sensing fibre. The optical pulses may have a frequency pattern as described in GB patent publication GB2,442,745 the contents of which are hereby incorporated by reference thereto, although DAS sensors relying on a single interrogating pulse are also known and may be used. Note that as used herein the term "optical" is not restricted to the visible spectrum and optical radiation includes infrared radiation and ultraviolet radiation. As described in GB2,442,745 the phenomenon of Rayleigh backscattering results in some fraction of the light input into the fibre being reflected back to the interrogator, where it is detected to provide an output signal which is representative of acoustic disturbances in the vicinity of the fibre. The interrogator therefore conveniently comprises at least one laser 112 and at least one optical modulator 114 for producing a plurality of optical pulses separated by a known optical frequency difference. The interrogator also comprises at least one photodetector 116 arranged to detect radiation which is Rayleigh backscattered from the intrinsic scattering sites within the fibre 104. A Rayleigh backscatter DAS sensor is very useful in embodiments of the present invention but systems based on Brillouin or Raman scattering are also known and could be used in embodiments of the invention.

The signal from the photodetector is processed by signal processor 108. The signal processor conveniently demodulates the returned signal based on the frequency difference between the optical pulses, for example as described in GB2,442,745. The signal processor may also apply a phase unwrap algorithm as described in GB2,442,745. The phase of the backscattered light from various sections of the optical fibre can therefore be monitored. Any changes in the effective optical path length within a given section of fibre, such as would be due to incident pressure waves causing strain on the fibre, can therefore be detected.

The form of the optical input and the method of detection allow a single continuous fibre to be spatially resolved into discrete longitudinal sensing portions. That is, the acoustic signal sensed at one sensing portion can be provided substantially independently of the sensed signal at an adjacent portion. Such a sensor may be seen as a fully distributed or intrinsic sensor, as it uses the intrinsic scattering processed inherent in an optical fibre and thus distributes the sensing function throughout the whole of the optical fibre. The spatial resolution of the sensing portions of optical fibre may, for example, be approximately 10 m, which for a continuous length of fibre of the order of 40 km say provides 4000 independent acoustic channels or so deployed along a 40 km section of transport network, such as a section of a rail network. This can provide effectively simultaneous monitoring of the entire 40 km section of track. In an application to train monitoring the individual sensing portions may each be of the order of 10 m in length or less.

As the sensing optical fibre is relatively inexpensive the sensing fibre may be deployed in a location in a permanent fashion as the costs of leaving the fibre in situ are not significant. The fibre may be deployed alongside or under the track (or road) and may for instance be buried alongside a section of track.

Figure 2:
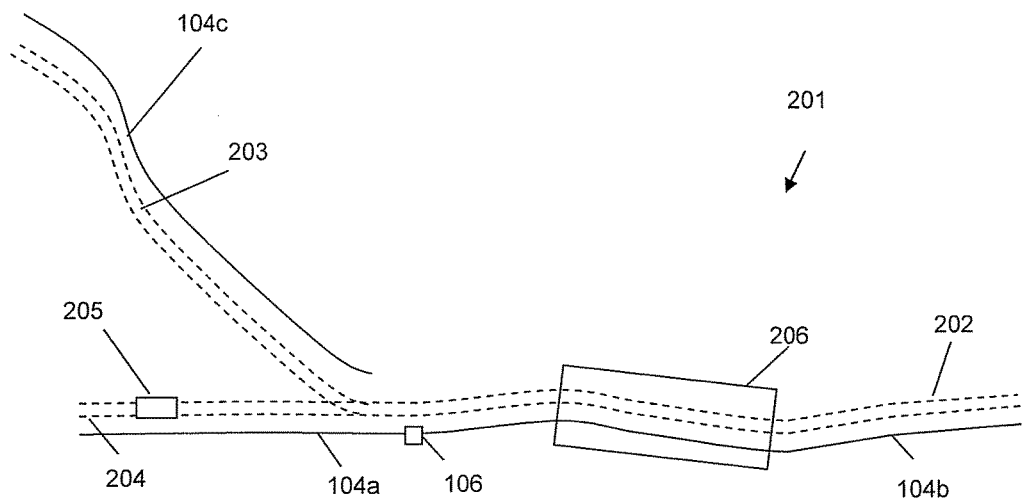
FIG. 2 illustrates a transport network been provided with DAS sensors.

FIG. 2 illustrates a section of traffic network, in this instance, a rail network 201, having optical fibre buried alongside the tracks. In this example the track has three braches 202, 203 and 204. As mentioned above fibre optic sensing can be performed on fibre lengths of the order of 40-50 km. However for some DAS sensors it can be difficult to reliably sense beyond 50 km or so along a fibre. A length of 40-50 km may be sufficient to monitor a desired section of track, say between main stations, and other fibres could be deployed to monitor other sections of track. For very long tracks it may be necessary to chain several DAS sensors together. FIG. 2 illustrates one interrogator unit 106 arranged to monitor one optical fibre 104a deployed along one part of the track (including part of braches 202 and 204) and another optical fibre 104b deployed along another length of track (branch 202). The interrogator unit could house two lasers and detectors etc., i.e. dedicated components for each fibre or the laser and possibly detector could be multiplexed between the two fibres. After 40 km say of fibre 104b another fibre could be deployed which is monitored by another interrogator unit. Thus there could be 80 km or so between interrogator units. In this example branch 203 is also monitored by a DAS sensor using a different sensing fibre 104c which is connected to a different interrogator unit (not shown).

In use the interrogator operates as described above to provide a series of contiguous acoustic sensing channels along the path of the track branches. In use the acoustic signals generated by a train 205 in motion along the track 204 may be detected and analysed to determine the exact train location and the speed.

As a significant length of track can be monitored by contiguous sensing portions of fibre it can relatively straightforward to detect train movement along the track. Clearly movement of the train will create a range of noises, from the engine noise of the locomotive, noises from the train cars and the couplings and noise from the wheels on the track. The acoustic signals will be greatest in the vicinity of the train and thus be looking at the intensity of the signals detected by the sensor the returns from the sensing portions of fibre adjacent the current position of the train will exhibit a relatively high acoustic intensity.

Embodiments of the present invention however may also use the acoustic signals detected by the DAS sensor(s) to provide condition monitoring of structure forming part of the network infrastructure. Such structures may especially be tunnels but may also be bridges, embankments or cuttings or the like, the integrity of which is important for safe operation of the network.

FIG. 2 illustrates a structure 206 which may comprise a tunnel through which branch 202 of the network runs. The optical fibre 104b also runs through the tunnel 206.

The movement of the train 205 towards and through tunnel 206 provides an acoustic stimulus to the tunnel which can be used to determine information about the condition of the tunnel.

Figure 3:
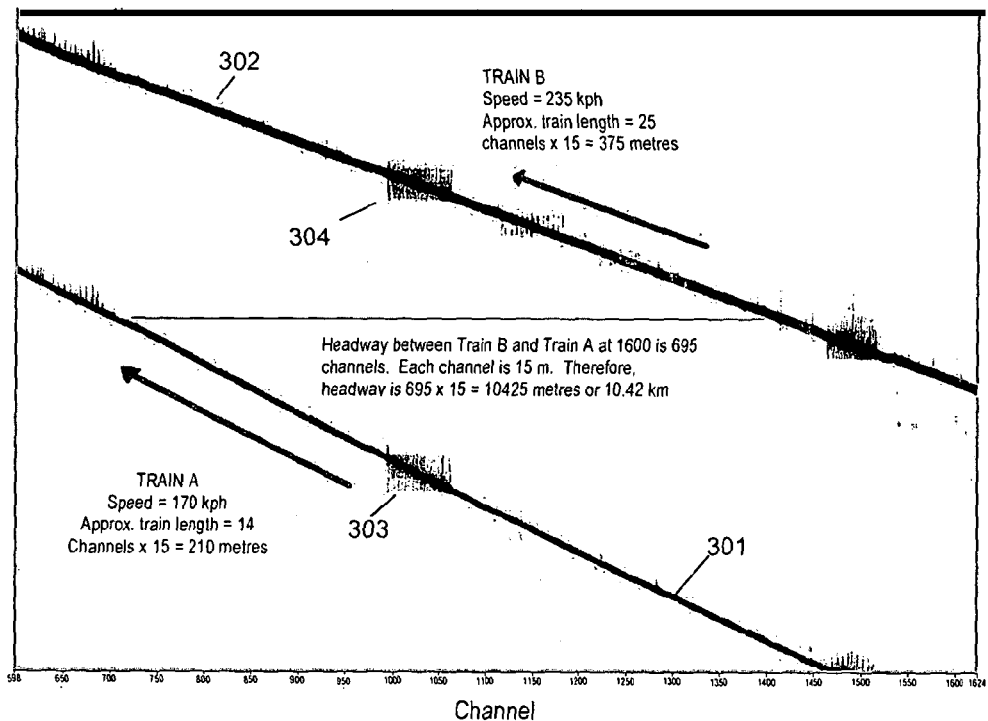
FIG. 3 shows data acquired from a DAS sensor monitoring trains moving on a section of track including a tunnel.

FIG. 3 illustrates some acoustic data obtained by performing some DAS sensing on an optical fibre deployed along a train track as trains traveled on the track. FIG. 3 shows a "waterfall plot" where the acoustic intensity from a selection of sensing channels over time is shown. The horizontal axis shows the various contiguous channels from a length of fibre. This data was acquired with a channel length of about 15 m. Time is illustrated in the vertical axis with more recent events at the top. In a typical waterfall plot the detected acoustic intensity may be illustrated by colour, however clearly FIG. 3 is black and white and acoustic intensity is represented by intensity of shade (with black being high intensity).

FIG. 3 illustrates a first series 301 of disturbances detected which are due to a first train travelling on the monitored section of track. It can be seen that the disturbances progress along the channels of the sensor in a fairly constant manner which is consistent with a train travelling at a relatively constant speed. Knowing that each channel of the sensor is 15 m in this example by looking at the rate of movement of the disturbances the speed of the train can be estimated. In effect the speed is the gradient of the series of disturbances.

FIG. 3 also shows a second series of disturbances 302, that, for a given channel, occur later in time. This indicates a second train also travelling on the monitored section of track behind the first train. By looking at the number of channels separating the two trains the distance between the trains, or headway, can be determined.

It will be seen that the acoustic disturbance due to the train is very intense for a number of sensing channels—which can be used to indicate the length of the train—however most the sensing channels are only excited as the train is actually passing by.

It can be seen however that there is an acoustic feature 303 in the first series of disturbances 301 where a number of sensing channels exhibit a response for a greater period of time as the train passes. A similar feature 304 can also be seen when looking at the second series of disturbances 302. These features correspond to the acoustic response of a tunnel.

It can be seen that as the acoustic disturbance due to the train reaches around channel 1075, there is a detectable response from channels 1075 to 990. It can be seen that these channels also exhibit a relatively strong response until the main intense disturbance due to the train has passed channel 990, which point the intensity of most of these channels quickly drops to normal background levels. The same general pattern occurs in both features 303 and 304.

Figure 4:
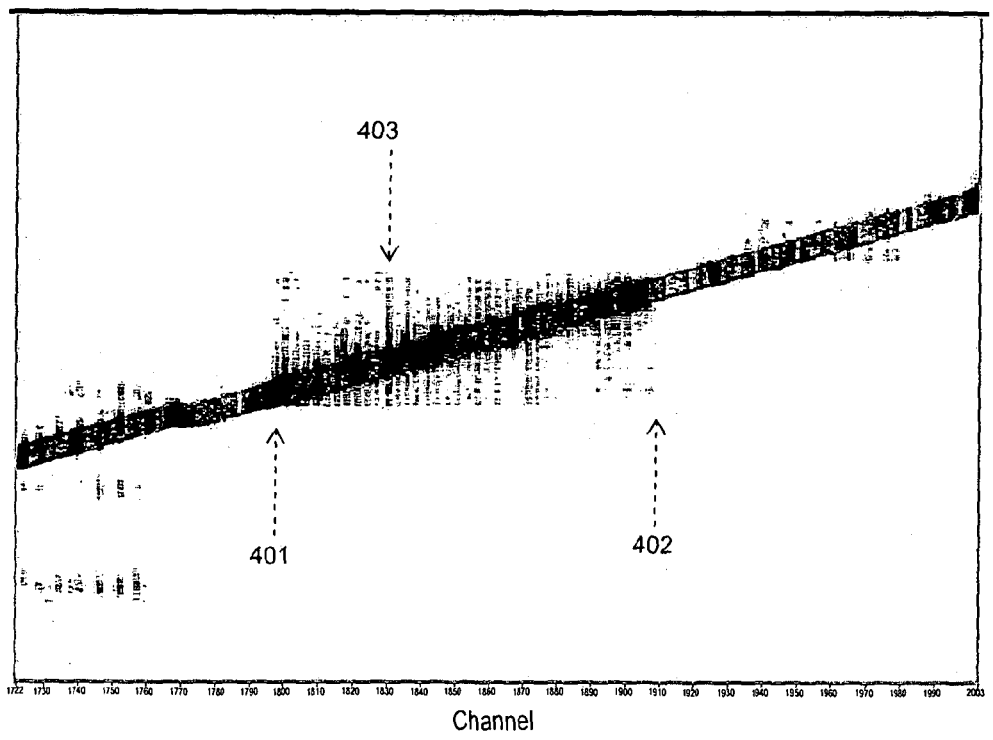
FIG. 4 shows more data acquired from a DAS sensor from a train passing a tunnel.

FIG. 4 shows the acoustic response from another monitored section of track with sensing fibre running through a tunnel in a bit more detail. FIG. 4 is a waterfall plot similar to FIG. 3 but shows a shorter section of monitored track, i.e. shows the response from the channels in more detail. In this plot the train was clearly moving along the track in a direction of increasing channel number.

Again it can be seen that the channels between positions 401 (about channel 1798) and 402 (about channel 1910) exhibit a prolonged acoustic response to the passage of the train. These 112 channels or sensing portions correspond to the section of optical fibre running through the tunnel. The tunnel length is thus about 1.68 km (with a channel width or length of sensing portion of 15 m).

It can also be seen that as the train reaches position 401, around channel 1798, that an acoustic signal spreads quickly along most of the channels of the tunnel. It will be seen however that the some channels exhibit much stronger responses than other channels. for example the channel indicated at 403 (around channel 1831) exhibit a relatively stronger response than other channels both before the train reaches that channel and after the train has passed that channel.

It can be seen that the disturbances due to the train actually passing a channel are very high and thus any pattern in the data from such channels is typically masked by the high intensity disturbances. But it can be seen that there is noticeable structure in the acoustic feature resulting from disturbances detected before and after the train has passed.

The acoustic response from the relevant channels which are acquired before and after the train passes may therefore be analysed to provide condition monitoring. For instance the data may be compared to data previously acquired to see if there are any significant changes. Thus referring to FIG. 4 if the relatively strong acoustic response at the channel indicated at position 403 was not present in any previous response this could indicate that something significant has changed in tunnel condition at this location. It will be noted that the detection of a possible anomaly also provides an indication of the location of such anomaly. Thus an inspection team could be dispatched to exactly the desired location.

The data used for comparison may comprise or be derived from a plurality of previously acquired acoustic responses. For example there may be an average response, or possible several average responses for different train types, speeds, weather conditions etc. The currently acquired data could be compared to the relevant previous data to detect any significant changes. If no significant changes are detected the current acquired response could be added to the body of previous data for use in comparison. If any significant changes are detected this could be used to generate an alert to a control room.

The comparison may involve comparing the pattern of intensity responses from the various sensing portions. As mentioned above definite structure can be seen in the response shown in FIG. 4. In addition however the data may be analysed by frequency to look for characteristic frequencies and/or the data may be analysed to detect the propagation of acoustic waves along the tunnel.

It can be seen from FIG. 4 that once the train reaches the start of the tunnel an acoustic signal propagates along the tunnel at relatively high speed. The propagation speed may be determined and/or the signals may be analysed to look for expected propagations speeds. For instance if the tunnel comprises a known material the returns could be analysed to look for signals propagating at such speeds.

It should be noted that the propagation speed of acoustic signals through the trackside structure, e.g. tunnels, is typically different to the propagation speed of acoustic signals through air or through the rails. The acoustic speed of propagation can be used to determine the signals corresponding to the structure.

The discussion so far has focussed on tunnels but the same techniques may be applied to other structures, such as bridges or other structures forming a portal, or in some instances other trackside structures. In this case the sensing fibre may not be simply laid to run through the tunnel but may be attached to the structure.

The structure to be monitored may thus be separate to and distinct from any structure, such as the rail track itself along which the vehicles directly travel.

Figure 5:
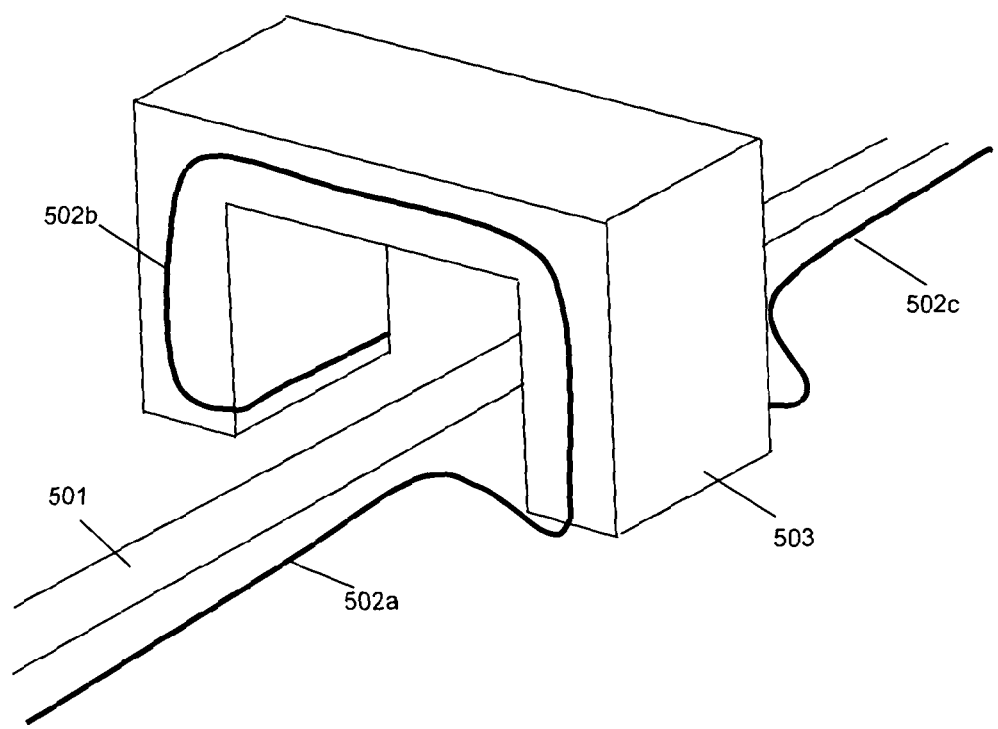
FIG. 5 illustrates how sensing fibre may be deployed upon a structure to be monitored.

FIG. 5 illustrates an example where a section 501 of transport network, such as a rail track, is provided with a sensing fibre 502. A first section 502a of sensing fibre is deployed to run alongside the path of the transport network and may be buried alongside the track as described previously. The track may run through a structure 503 which it is wished to monitor the condition of, for example a bridge. At this point the optical fibre may emerge from the ground and may be deployed to monitor the structure. A second section 502b of fibre may therefore be arranged to be attached to the structure. As shown in FIG. 5 the fibre may be arranged to run alongside the bridge and then loop back again. The rest of the fibre 502c may then be deployed to run along the path of the network 501.

The section of fibre which is deployed on the structure may be any suitable length but may be arranged to be at least as long as two sensing portions of the DAS sensor so as to ensure that at least one sensing portion falls entirely within the section of fibre deployed on the structure.

In general the fibre may be attached to the structure by any suitable means, however in some instances it may be possible to embed a fibre into the material of the structure itself. Such a fibre may therefore be a dedicated fibre for monitoring the structure or may again form part of the monitoring for of the transport network.

Figure 6A:
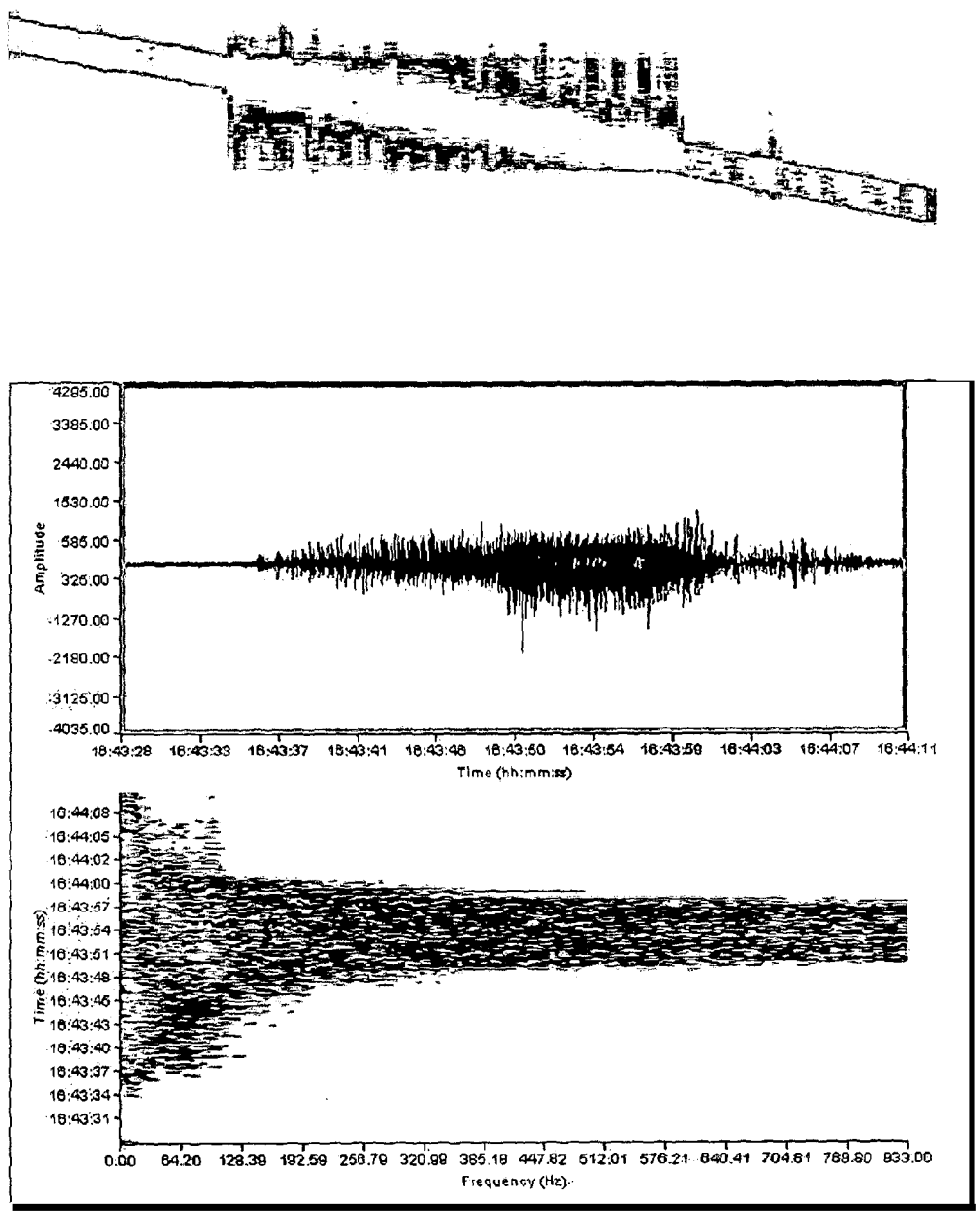
FIG. 6 illustrates data acquired from a DAS sensor on a rail network from monitoring trains passing a viaduct, a tunnel and a bridge.
Figure 6B:
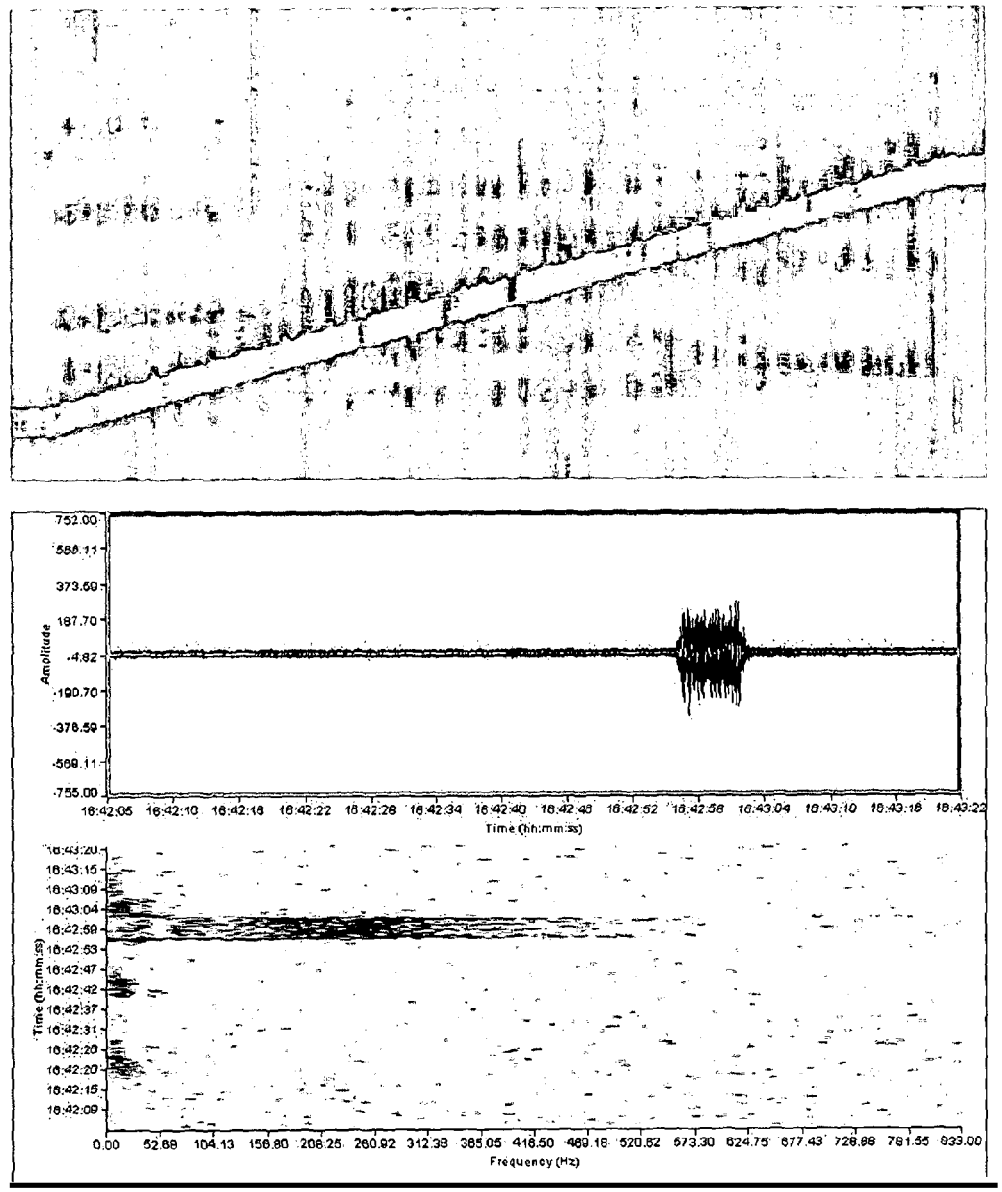
Figure 6C:
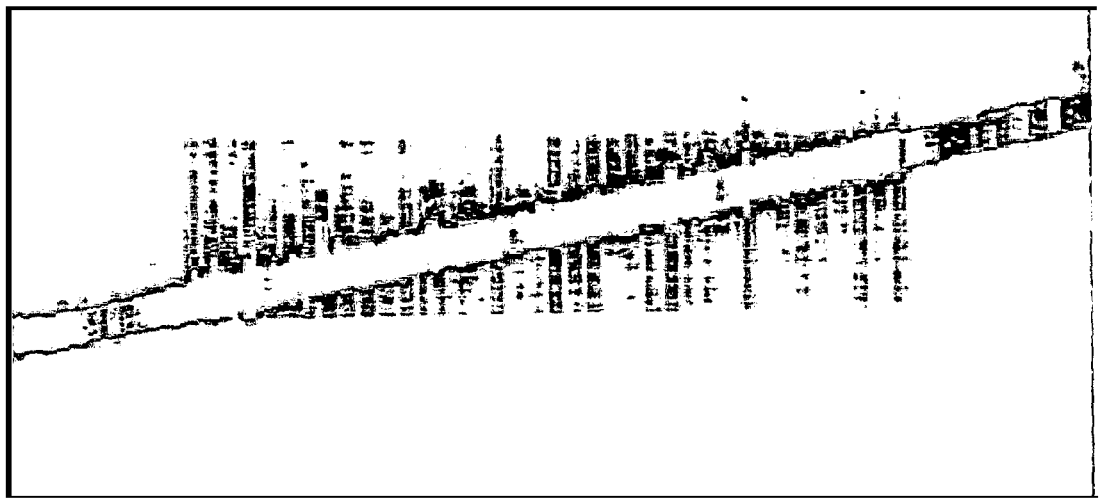
Figure 6C:
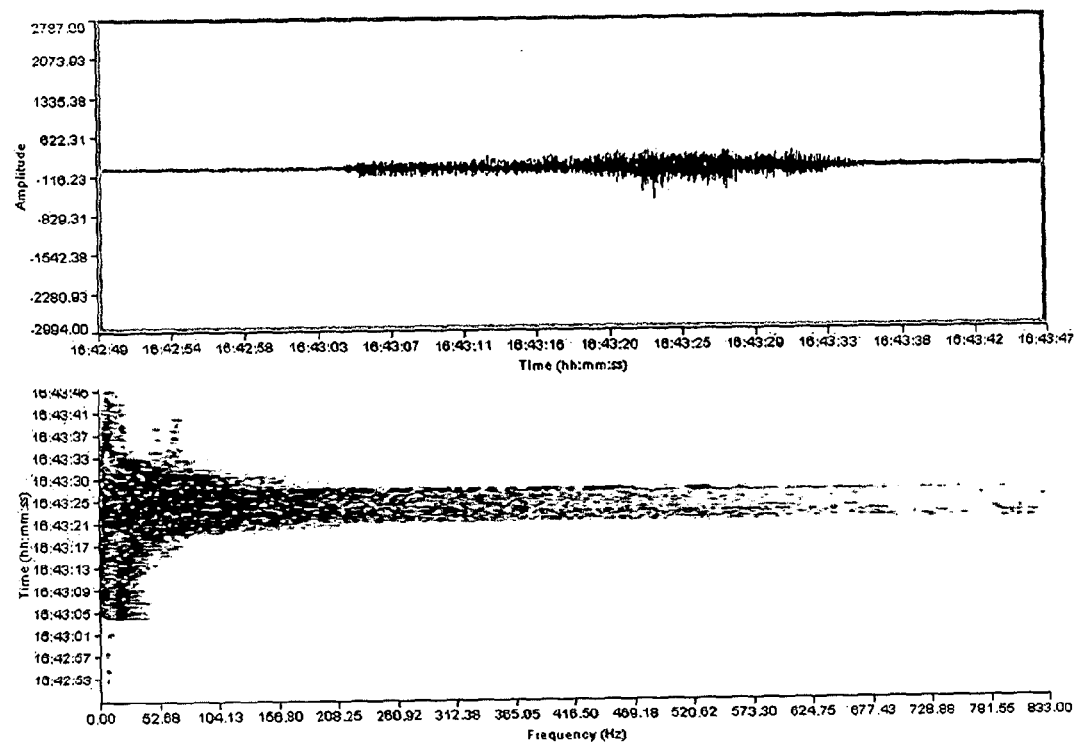

FIGS. 6a to 6c shows some further data acquired from a DAS sensor having sensing fibre laid along a rail network as trains pass by infrastructure of the rail network, namely a viaduct, a bridge and a tunnel. In each case the top plot shows a waterfall diagram of acoustic intensity along the sensing channels of the optical fibre against time (intensity being represented by colour in an actual display) along with an analysis of the various components making up the acoustic signals detected.

In each case relatively intense signals distinct from the main noise associated with the train itself can be detected and acoustic signals travelling up and down the relevant structure at propagation speeds different to propagation in air or the rails can be detected.

The same techniques may also be applicable to other transport networks. For instance a road network may have fibre laid along the road which is used for DAS sensing and such fibre may pass under bridges or through tunnels. The acoustic response to traffic moving on the road may be monitored. It will be appreciated that road traffic may not as spread out as rail traffic so there may be a more constant stimulus during busy road periods which may disguise the acoustic response of the structure. However the DAS sensing fibre may be constantly monitored and there may be periods of light use, for instant at night, where individual traffic passes and the acoustic response can be detected in a similar fashion to that described above.

In general then the embodiments of the present invention provide low cost methods for remote condition monitoring that provides good spatial coverage, even for long tunnels and the like and which uses the normal movement of traffic on the network to provide an acoustic stimulus to the structure being monitored.

The invention claimed is:

1. A method of condition monitoring of a structure forming part of a transport network comprising:
   performing distributed acoustic sensing on one or more optical fibres deployed to monitor said structure to provide a measurement signal from each of a plurality of acoustic sensing portions;
   analysing the measurement signals generated from movement of traffic on the transport network in a vicinity of said structure to identify acoustic signals associated with said structure; and
   analysing said acoustic signals associated with said structure to provide an indication of any changes in condition of said structure; wherein analysing said acoustic signals associated with said structure comprises identifying acoustic waves propagating in the structure and analysing the propagation speeds of acoustic waves in the structure.

2. A method as claimed in claim 1 wherein analysing said acoustic signals associated with said structure comprises comparing the acoustic signals with previously acquired acoustic signals.

3. A method as claimed in claim 1 comprising identifying any discontinuities in acoustic waves propagating in the structure.

4. A method as claimed in claim 1 comprising identifying acoustic waves propagating at different speeds in the structure.

5. A method as claimed in claim 1 wherein the acoustic signals associated with said structure comprise acoustic signals detected by the sensing portions before and/or after the traffic movement past the relevant sensing portion.

6. A method as claimed in claim 1 wherein the acoustic signals associated with said structure comprise a low frequency response.

7. A method as claimed in claim 1 further comprising performing distributed acoustic sensing on said one or more optical fibres to track the movement of traffic on the transport network.

8. A method as claimed in claim 7 wherein at least part of said one or more optical fibres is deployed along a path of the transport network.

9. A method as claimed in claim 8 wherein a first optical fibre of said one or more optical fibres has at least a first section deployed along the path of the transport network and at least a second section deployed to monitor said structure.

10. A method as claimed in claim 9 wherein the second section of the first optical fibre is attached to the structure.

11. A method as claimed in claim 1 wherein the transport network is a rail network.

12. A method as claimed in claim 11 wherein said structure comprises a tunnel.

13. A method as claimed in claim 12 wherein said one or more optical fibres comprises at least one optical fibre deployed alongside a rail track running through the tunnel.

14. A method as claimed in claim 13 wherein said structure comprises the rail track.

15. A method of condition monitoring of a structure forming part of a transport network, the method comprising:
   receiving a plurality of measurement signals acquired by a one or more distributed acoustic sensors having one or more optical fibres deployed to monitor said structure;
   analysing the measurement signals generated from movement of traffic on the transport network in a vicinity of said structure to identify acoustic signals associated with said structure; and
   analysing said acoustic signals associated with said structure to provide an indication of any changes in condition of said structure; wherein analysing said acoustic signals associated with said structure comprises identifying acoustic waves propagating in the structure and analysing the propagation speeds of acoustic waves in the structure.

16. A distributed acoustic sensing system comprising:
   an interrogator unit for, in use, performing distributed acoustic sensing on one or more optical fibres deployed to monitor a structure of a transport network to provide a measurement signal from each of a plurality of acoustic sensing portions; and
   a processor configured:
      to analyse the measurement signals generated from movement of traffic on the transport network in a vicinity of said structure to identify acoustic signals associated with said structure; and
      analyse said acoustic signals associated with said structure to provide an indication of any changes in condition of said structure by identifying acoustic waves propagating in the structure and analysing the propagation speeds of acoustic waves in the structure.

17. A distributed acoustic sensing system according to claim 16 comprising at least one optical fibre deployed to monitor the structure.

18. A distributed acoustic sensing system according to claim 17 wherein at least part of said at least one optical fibre is deployed along a path of the transport network.

19. A distributed acoustic sensing system according to claim 18 wherein the transport network is a rail network.

20. A distributed acoustic sensing system according to claim 19 wherein the system is configured to monitor the condition of one or more tunnels on the transport network.

* * * * *